US00PP33649P2

(12) United States Plant Patent
Holtmaat

(10) Patent No.: US PP33,649 P2
(45) Date of Patent: Nov. 16, 2021

(54) ***ECHINACEA* PLANT NAMED 'CARROT489'**

(50) Latin Name: ***Echinacea* hybrid**
Varietal Denomination: CARROT489

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 17/185,910

(22) Filed: Feb. 25, 2021

(30) Foreign Application Priority Data

Oct. 8, 2020 (QZ) ..... 2020/2458

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — Penny J. Aguirre

(57) ABSTRACT

A new cultivar of *Echinacea* plant named 'CARROT489' that is characterized by its inflorescences with ray florets and disc florets that are orange-red in color, its strong stems, and its conspicuous disc florets.

2 Drawing Sheets

Botanical classification: *Echinacea* hybrid.
Variety denomination: 'CARROT489'.

CROSS REFERENCE TO A RELATED APPLICATION

This application claims priority to European Community Plant Variety Office (CPVO) Plant Breeder's Rights Application No. 2020/2458 filed on Oct. 8, 2020, under 35 U.S.C. 119(f), the entire contents of which is incorporated by reference herein.

BACKGROUND OF THE INVENTION

The present invention relates to a new and distinct cultivar of *Echinacea* of hybrid origin and will be referred to hereafter by its cultivar name, 'CARROT489'. 'CARROT489' represents a new cultivar of coneflower, an herbaceous perennial grown for landscape use.

The new cultivar arose from an ongoing breeding program by the Inventor in Zuidwolde, The Netherlands with the objective of selecting new cultivars of *Echinacea* with strong plant habits, unique inflorescence colors and enlarged disc florets. The new cultivar was selected as a unique seedling in a trial field by the Inventor in July of 2019. The trial field had been planted with seed collected from numerous cultivars and proprietary *Echinacea* seedlings from the Inventor's breeding program. The parentage of 'CARROT489' is therefore unknown.

Asexual propagation of the new cultivar was first accomplished by tissue culture using meristematic tissue in Heerhugowaard, The Netherlands in July of 2019 under the direction of the Inventor. Asexual propagation by tissue culture has determined that the characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'CARROT489' as a unique cultivar of *Echinacea*.

1. 'CARROT489' exhibits inflorescences with ray florets and disc florets that are orange-red in color.
2. 'CARROT489' exhibits strong stems.
3. 'CARROT489' exhibits conspicuous disc florets.

The new cultivar can be most closely compared to the cultivars 'Marmalade' (U.S. Plant Pat. No. 22,602) and 'Eccentric' (U.S. Plant Pat. No. 23,979). 'Marmalade' and 'Eccentric' are both similar to 'CARROT489' in inflorescence shape. 'Marmalade' differs from 'CARROT489' in having ray florets that are grey-yellow in color, a taller plant height, a more open plant habit, and disc florets that are red in color. 'Eccentric' differs from 'CARROT489' in having ray, disc florets that are red in color, and a taller plant height.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited to website listings by AB Cultivars, Hogendoorn, Dobrepole, Rosliny od Ogrodnika, Hortensia, and Flowerbulbs-Cebulki Kwiatowe.

BRIEF DESCRIPTION OF THE DRAWINGS

The plants in the accompanying photographs depict the characteristics of a two-year-old plant of 'CARROT489' as grown in a 17-cm container in Zuidwolde, The Netherlands.

The photograph in FIG. 1 provides a side view of 'CARROT489' in bloom.

Figure 1:
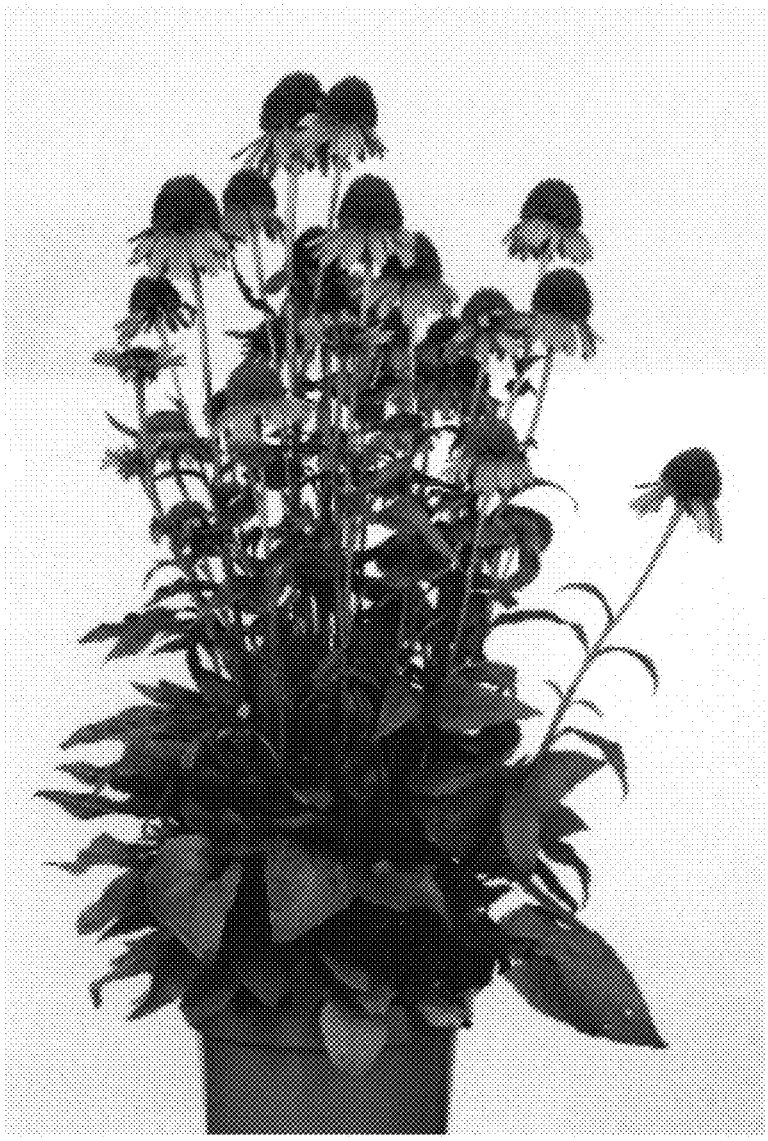
Figure 2:
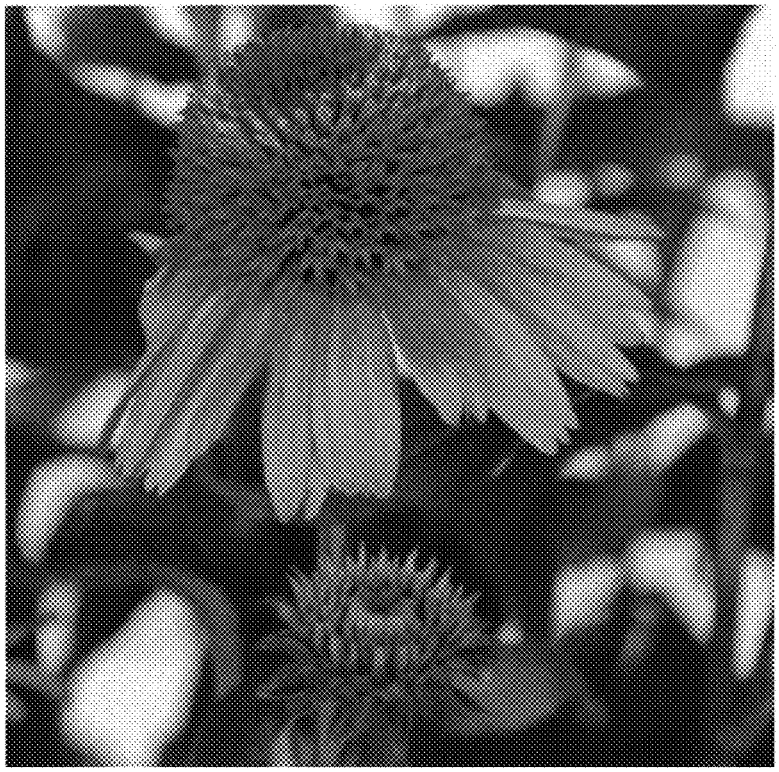

The photograph in FIG. 2 provides a close-up view of an inflorescence of 'CARROT489'.

Figure 3:
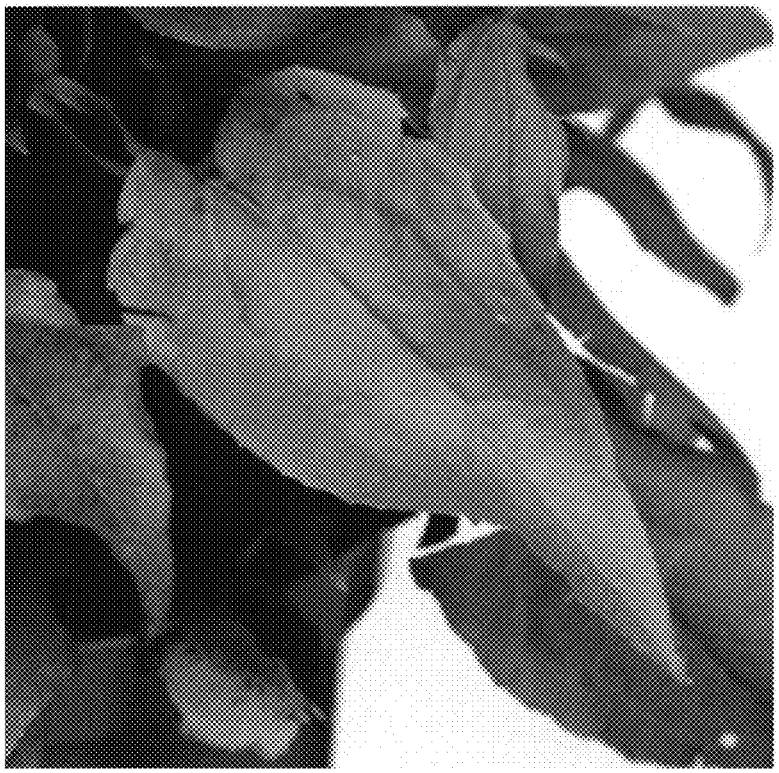

The photograph in FIG. 3 provides a close-up view of a leaf of 'CARROT489'.

The colors in the photograph may differ slightly from the color values cited in the detailed botanical description, which accurately describe the colors of the new *Echinacea*.

BOTANICAL DESCRIPTION OF THE PLANT

The plants in the accompanying photographs depict the characteristics of two-year-old plants of 'CARROT489' as grown in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Approximately 10 weeks from summer and late summer (July until late September) in The Netherlands.

*Plant type*.—Herbaceous perennial.

*Plant shape*.—Oblong to ovate.

*Plant habit*.—Clump forming and upright with strong stems.

*Height and spread*.—Average of 58.1 cm in height, 40.5 cm in width.

*Hardiness*.—U.S.D.A. Zones 4 to 9.

*Diseases and pests*.—No resistance or susceptibility to pests or diseases has been observed.

*Root description*.—Fibrous.

*Propagation*.—Tissue culture.

*Root development*.—An average of 10 weeks for root development with a finished plant produced in about 3 months.

*Growth rate*.—Moderately vigorous.

Stem description:

*Shape*.—Rounded.

*Stem color*.—146A.

*Stem size*.—Average of 3.5 mm in diameter and an average of 36 cm in length.

*Stem surface*.—Rough to the touch, moderately covered with short strigose hairs; 0.2 mm in length, matches surface color.

*Stem strength*.—Strong.

*Stem aspect*.—Stems grow in an average angle of 10° from the base (0°=vertical).

*Branching*.—Main flowering stems grow from the base with a few lateral branches present, average of 25 primary branches, 1 to 2 lateral branches per primary stem.

Foliage description:

*Leaf shape*.—Narrow ovate.

*Leaf division*.—Simple.

*Leaf base*.—Attenuate.

*Leaf apex*.—Narrowly acute.

*Leaf venation*.—Pinnate, upper surface; 151C, lower surface; 152D.

*Leaf margins*.—Entire, moderately coarsely undulate.

*Leaf attachment*.—Petiolate.

*Leaf arrangement*.—Alternate.

*Internode length*.—An average of 7.2 cm.

*Leaf size*.—Basal leaves; 12.6 cm in length, 5.8 cm in width, cauline leaves; 8.8 cm in length, 4.1 cm in width.

*Leaf color*.—Young upper surface; 143A, young lower surface; 146B, mature upper surface; NN137B, mature lower surface; 146B.

*Leaf surface*.—Both surfaces are slightly glossy, rough to the touch and moderately covered with very short strigose hairs; average length of 0.2 mm, too small to measure color.

*Petioles*.—On basal leaves an average of 12 cm in length and 3 mm in diameter, on cauline stem leaves V-shaped an average of 1.7 cm in length and 3 mm in diameter, surface is smooth and moderately covered with very short strigose hairs 0.2 mm in length and too small to measure color, color; upper surface 144A, main vein 151A to 151B, basal leaves changing to N186C at the proximal end, lower surface 144A.

Inflorescence description:

*Type*.—Terminal capitulum, heterogamous with ray florets around the head margin and anemone-type disc florets in the center.

*Capitulum number*.—One terminal capitulum per lateral branch.

*Lastingness of inflorescence*.—About four weeks.

*Capitulum size*.—Matures to about 4.1 cm in height and 6.7 cm in diameter, disk size is an average of 3.4 cm in diameter.

*Fragrance*.—None.

*Involucral bracts or phyllary*.—Average of 48 arranged in 3 rows, up to 9 mm in length and 2 mm in width, cuneate base, acute apex, narrow ovate in shape, very slightly pointed downward, entire margins moderately, held in an average angle of -45° to horizontal, color; upper surface 137B, lower surface 138B, upper surface smooth, glabrous, matte, lower surface smooth, matte, sparsely covered with very short hairs, margins moderately covered with very short hairs, average length of hairs 0.2 mm, too small to measure color.

*Buds*.—Flattened globular in shape, up to 1.8 cm in diameter and 1.5 cm in length, color; 146A to 146B, immature ray florets 173C to 173D.

*Peduncle*.—Strong, straight on top of main (flowering) stem, average of 10.8 cm in length, 4.5 mm in diameter, color; 146C, surface is moderately covered with very short hairs an average length of 0.2 mm in length, too small to measure color.

*Ray florets*.—Rotate, average of 24 (varying between 20 and 31), whorled, oblanceolate in shape, average of 3.4 cm in length and 9 mm in width, praemorse apex, cuneate base, entire margin, moderately drooping in an average angle of −45° , upper surface matte, velvety and glabrous, lower surface very slightly glossy, sparsely pubescent, color; upper surface when opening N25A, lower surface when opening 51B to 51C, upper surface when fully open 31A, changing to 45C at the base, lower surface when fully open 54C, upper surface fading to 37A, changing to N34C at the base, lower surface fading to 54C.

*Disc florets*.—Numerous, average of 120, tubular, lower 75% fused, base fused into tube, arranged spirally on disc, average of 1.3 cm in length and 3.5 mm in width, entire margin, both surfaces glabrous, slightly glossy, color; upper surface when opening 47A, mid-section and base 21C, lower surface when opening 47A, mid-section 20B to 20C, base 53C to 53D, upper surface fully open 33B, lower surface fully open 47D.

*Receptacle*.—Narrow ovate to narrow deltoid in shape, average of 1 cm in height and 5 mm in diameter, NN155A in color.

*Receptacle spines*.—An average of 120 per disc floret, acicular in shape, acute apex, attenuate base, 1.2 cm in length, 2 mm in diameter, glabrous and glossy surface, color: apex; N45A, mid-section; 30B, base; 144A to 144B.

Reproductive organs (present on disc florets only):

*Gynoecium*.—Pistil; 1, 5.5 mm in length, stigma; unequal, decurrent, 4 mm in length, 153A, style; 4 mm in length and 150D in color, ovary; 157C in color.

*Androecium*.—Stamens; 5, filaments; 2 mm in length, 157D in color, anther; linear in shape, 3 mm in length and N200A to N200B in color, pollen; moderate, 23A in color.

*Fruit/seed*.—No fruit or seed detected to date.

It is claimed:

1. A new and distinct cultivar of *Echinacea* plant named 'CARROT489' substantially as herein illustrated and described.

* * * * *